(12) United States Patent
Bonile

(10) Patent No.: US 6,702,730 B2
(45) Date of Patent: Mar. 9, 2004

(54) MAGNETIC BED DEVICE AND METHOD FOR ENHANCED BODY FUNCTION

(76) Inventor: Dean R Bonile, 109-5421 11th ST N.E., Calgary AB (CA), T2E 6M4

( * ) Notice: Subject to any disclaimer, the term of this patent is extended or adjusted under 35 U.S.C. 154(b) by 0 days.

(21) Appl. No.: 10/051,005

(22) Filed: Jan. 22, 2002

(65) Prior Publication Data

US 2002/0198434 A1 Dec. 26, 2002

Related U.S. Application Data

(60) Provisional application No. 60/262,970, filed on Jan. 22, 2001.

(51) Int. Cl.[7] .............................. A61N 2/00; A47C 17/00
(52) U.S. Cl. ................................. 600/9; 5/693
(58) Field of Search .................. 600/9, 15; 5/421, 5/490, 693, 701, 736, 906, 591; 607/114, 96, 149

(56) References Cited

U.S. PATENT DOCUMENTS

| | | | |
|---|---|---|---|
| 237,939 A | * 2/1881 | Wilson | 600/15 |
| 272,904 A | * 2/1883 | Russell | 600/15 |
| 3,921,620 A | * 11/1975 | Nakayama | 600/15 |
| 4,143,435 A | * 3/1979 | Masuda | 5/693 |
| 4,330,892 A | * 5/1982 | Fukushima | 5/636 |
| 4,509,219 A | * 4/1985 | Yagi | 5/693 |
| 4,587,956 A | * 5/1986 | Griffin et al. | 600/15 |
| 5,017,185 A | * 5/1991 | Baermann | 600/15 |
| 5,226,185 A | * 7/1993 | Guay et al. | 5/693 |
| 5,738,624 A | * 4/1998 | Zablotsky et al. | 600/9 |
| 5,788,624 A | * 8/1998 | Lu et al. | 600/9 |
| 6,048,303 A | * 4/2000 | Porter | 600/15 |
| 6,139,486 A | * 10/2000 | Matuszewski et al. | 600/15 |
| 6,155,967 A | * 12/2000 | Catlett | 600/15 |

\* cited by examiner

*Primary Examiner*—Eric F. Winakur
(74) *Attorney, Agent, or Firm*—Pillsbury Winthrop LLP

(57) ABSTRACT

A magnetic bed device designed to be placed adjacent to a mattress having a surface configured to support a resting person is provided. The magnetic bed device includes a plurality of magnets that produce a negative magnetic field in a region adjacent the surface, and a positive magnetic field in a region remote from the surface. The plurality of magnets are positioned relative to the surface such that only the negative magnetic field extends beyond the surface to the resting person. In another embodiment, a magnetic bed device for supporting a resting person is provided. The magnetic bed device includes a supporting layer having a surface configured to support the resting person and the plurality of magnets positioned relative to the surface such that only the negative magnetic field extends beyond the supporting layer to the resting person. In yet another embodiment, a magnetic bed device is provided that includes the supporting layer and a magnetic field generator disposed within the supporting layer. The magnetic field generator is configured to provide a negative magnetic field that prevents a positive or reversed direction of magnetic flux from entering the resting person. A method of enhancing body function of a resting person is also provided. The method includes positioning a magnetic device that produces a negative magnetic field beneath the supporting layer configured to support the resting person.

35 Claims, 10 Drawing Sheets

MAGNETIC BED DEVICE AND METHOD FOR ENHANCED BODY FUNCTION

CROSS REFERENCE TO RELATED APPLICATIONS

The present application claims priority to U.S. Provisional Application No. 60/262,970 filed Jan. 22, 2001, the entirety of which is hereby incorporated into the present application by reference.

BACKGROUND OF THE INVENTION

1. Field of Invention

This invention relates to enhancement of body function using magnetic fields. More specifically, the invention relates to a magnetic bed device that uses a negative magnetic field to prevent cancer and to treat fibromyalgia, osteoporosis, orthopedic injury or other disease.

2. Description of Background Information

A growing body of scientific literature exists demonstrating biological effects of static magnetic fields to treat disease. Generally, magnetic bed devices and other static magnetic products use static magnetic fields to treat pain experienced by a person, to promote circulation of the person's blood, to relieve fatigue by freeing stiffness in the person's muscles and to complement therapy for persons with certain disease, such as fibromyalgia, cancer, osteoporosis and orthopedic injury. Such static magnetic products have recently gained considerable popularity among consumers.

SUMMARY

One aspect of embodiments of the present invention is to provide a magnetic bed device that prevents positive or reversed direction of magnetic flux from entering a resting person's body, for example, while the person is resting or sleeping.

Another aspect of embodiments of the present invention is to provide a magnetic bed device configured to support a resting person. The magnetic bed device includes a mattress or supporting layer having a surface configured to support the resting person and a magnetic device comprising a plurality of magnets constructed and arranged to produce a negative magnetic field in a region adjacent the surface. The plurality of magnets is constructed and arranged to produce a positive magnetic field in a region remote from the surface. The plurality of magnets is positioned relative to the surface such that only the negative magnetic field extends beyond the supporting layer to the resting person.

Yet another aspect of embodiments of the present invention is to provide a magnetic device comprising a plurality of magnets constructed and arranged to produce a negative magnetic field in a region adjacent to a surface configured to support a resting person. The plurality of magnets is constructed and arranged to produce a positive magnetic field in a region remote from the surface. The plurality of magnets is positioned relative to the surface such that only the negative magnetic field extends beyond the supporting layer.

A further aspect of embodiments of the present invention is to provide a method of producing a body function enhancing field. The method comprises positioning a magnetic device beneath a supporting layer configured to support a resting person. The magnetic device comprises a plurality of magnets that produce a negative magnetic field in a region adjacent the supporting layer, and a positive magnetic field in a region remote from the supporting layer. The plurality of magnets is positioned relative to the supporting layer such that only the negative magnetic field extends beyond the supporting layer. In other embodiments or implementations, the method may further comprise positioning the resting person on the supporting layer within the negative magnetic field.

Other objects, features and advantages of the present invention will become apparent from the following detailed description, the accompanying drawings, and the appended claims.

BRIEF DESCRIPTION OF THE DRAWINGS

The present invention is further described in the detailed description which follows, by reference to the noted drawings by way of non-limiting exemplary embodiments, in which like reference numerals represent similar parts throughout the several views of the drawings, and wherein.

DETAILED DESCRIPTION OF EMBODIMENTS OF THE PRESENT INVENTION

Figure 1:
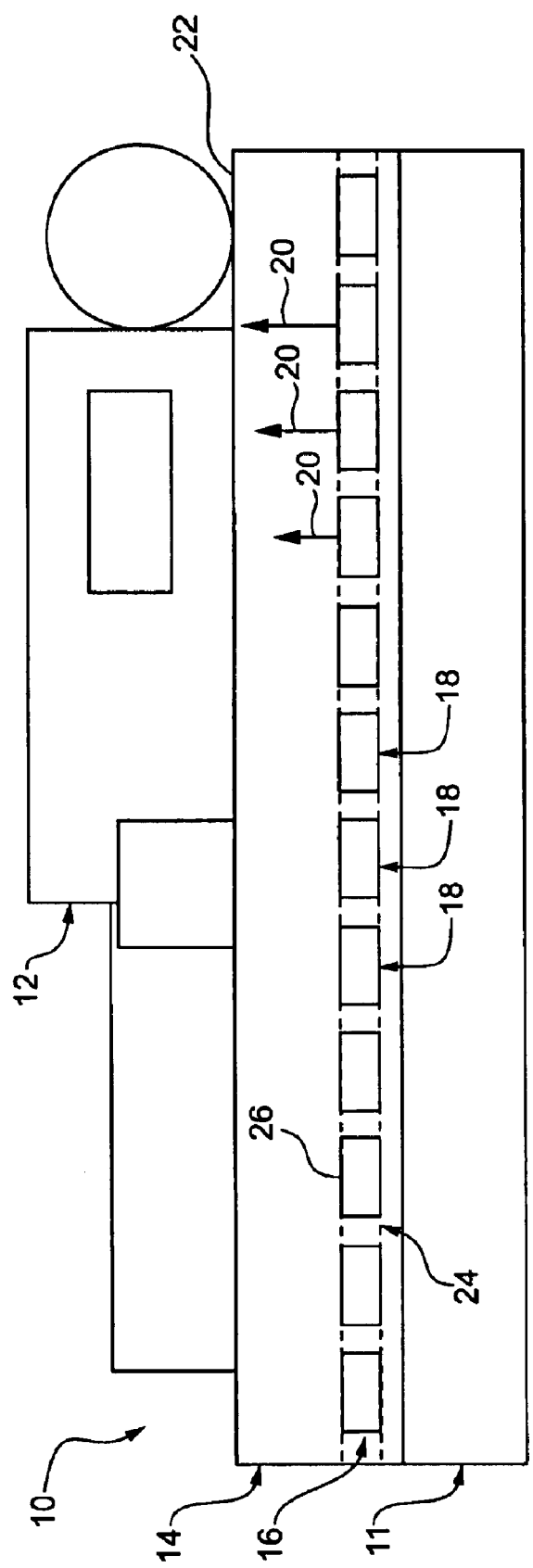
FIG. 1 is a schematic diagram of a magnetic bed device for a person in accordance with the principles of the invention.

Referring to FIG. 1, in accordance with the present invention, there is provided a magnetic bed device 10 to support a resting person 12. The magnetic bed device 10 uses a negative magnetic field 20 to prevent the resting person 12 from experiencing a positive or reversed direction of magnetic flux. Though the detailed description focuses on treatment of a person, it is contemplated that other animals could benefit from treatment in accordance with the present invention.

The magnetic bed device 10 includes a supporting layer 14 having an upper surface 22 configured to support the resting person 12 and a boxspring 11. The boxspring 11 is positioned beneath the supporting layer 14 and the magnetic bed device 10 for supporting the same. A magnet group, generally indicated at 16, includes a plurality of magnets 18 that are constructed and arranged to produce the negative magnetic field 20. The magnet group 16 is positioned relative to the magnetic bed device 10 and the boxspring 11 such that the negative magnetic field 20 extends beyond the magnetic bed device 10 to the resting person 12. The negative magnetic field 20 enhances the person's immune system, reduces stress and fatigue, and helps treat or prevent disease, such as, for example, cancer, fibromyalgia, osteoporosis, orthopedic injury, and other disease.

As shown in FIG. 1, at least one of the magnetic bed device 10 and the supporting layer 14 is configured to receive and support the person 12 when the person 12 is resting on the magnetic bed device surface 22. In one implementation of the magnetic bed device 10, the person 12 can be exposed to the negative magnetic field 20 while sleeping or resting on the supporting layer 14, for example. Although not shown in this embodiment, the supporting layer 14 or the magnetic bed device 10 may include resilient material, such as plastic or foam. The resilient material can be interspersed throughout at least one of the supporting layer 14 and the magnetic bed device 10 to provide a supporting force such that the resting person 12 is supported above a highest extending portion of the positive magnetic field. The resilient material could be interspersed throughout at least one of the supporting layer 14 and the magnetic bed device 10, and can be arranged in a plurality of vertically and horizontally extending rows and columns, for example. The resilient material can be made from metal or any other material such that the resilient material allows the negative magnetic field to extend beyond the magnetic bed device surface 22 of the supporting layer 14 and prevents the positive magnetic field from extending to the resting person. In general, the resilient material is formed into springs, but may be formed into any other configuration that provides a sufficient supporting force to support the resting person.

Figure 2:
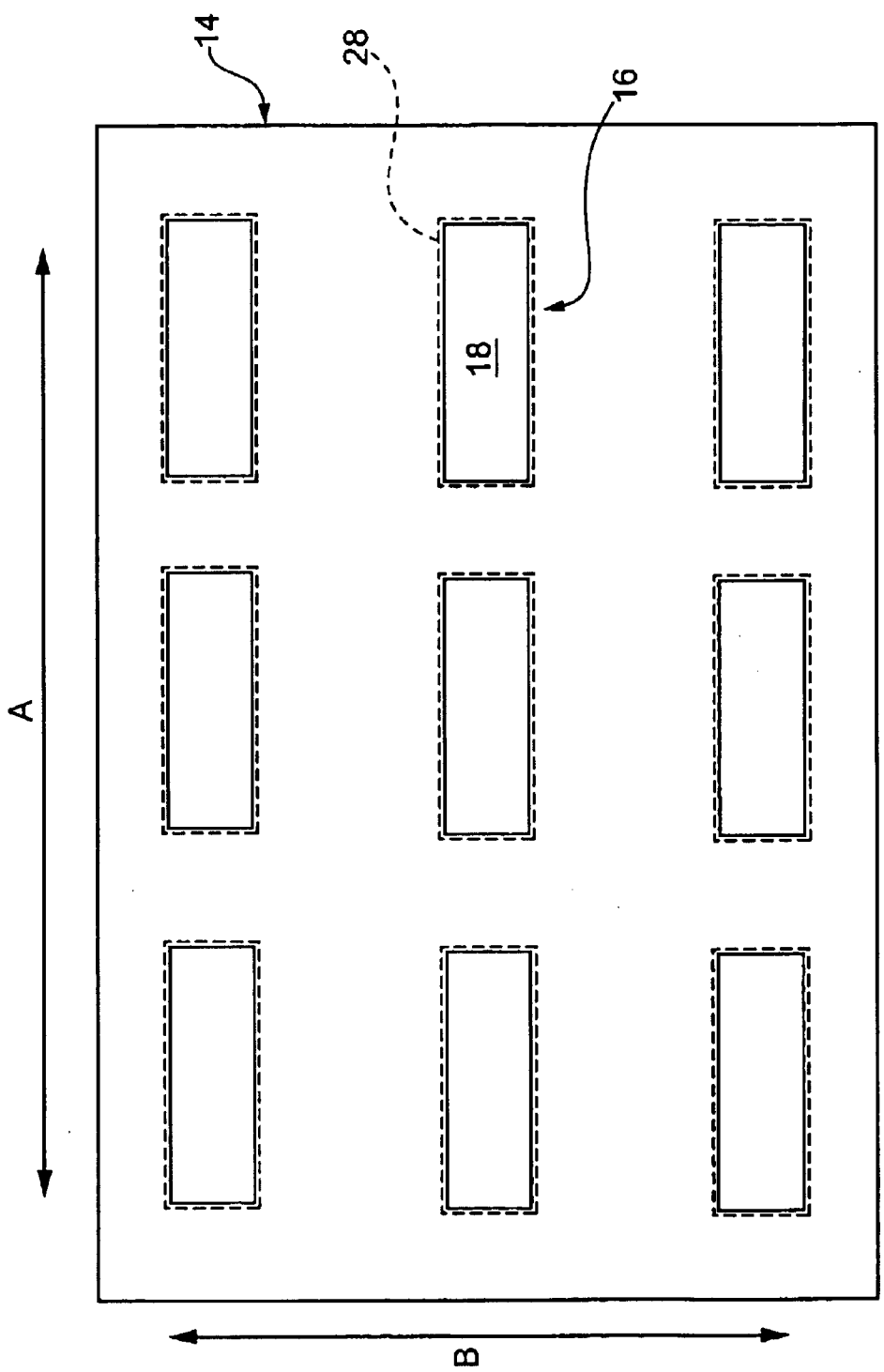
FIG. 2 is a top plan view of the magnetic bed device of FIG. 1 with certain portions removed so as to show a magnetic device comprising a plurality of magnets used to provide a negative magnetic field.

The magnets 18 constitute a magnetic field generator and can include permanent magnets having a positive pole (or North magnetic pole) 24 and a negative pole (or South magnetic pole) 26. The magnets 18 can be oriented so that the negative poles 26 face the person 12 to uniformly provide the negative magnetic field 20. FIG. 2 shows each magnet 18 being spaced from adjacent magnets 18 in both a X direction (as represented by the double-arrow indicated as A) and a Y direction (as represented by the double-arrow indicated as B) of the supporting layer 14 by a predetermined distance, such as, for example, 2.00 inches or to as little as 0.05 inches.

Each magnet 18 can be positioned relative to the magnetic bed device 10 and the boxspring 11 such that the person 12 is exposed to an appropriate amount of negative magnetic field 20 when the person 12 rests on the magnetic bed device 10. The strength of the negative magnetic field 20 may be on the order of several Gauss, such as, for example, 2–30 Gauss, which is uniformly provided across the magnetic bed device surface 22. Alternately, the magnets 18 can be electromagnets configured to provide the negative magnetic field 20 of appropriate strength and configuration.

To retain the magnets 18 in at least one of the supporting layer 14 and the magnetic bed device 10, the supporting layer 14 or the magnetic bed device 10 can include a magnet retaining structure 24, for example, in the form of cutout pockets or recessed portions. The magnet retaining structure 24 is configured to orient the magnets 18 in the same direction (e.g., with the negative poles 26 facing a lower back surface of the person 12) at a predetermined distance from the person 12, such as, for example, 3–20 inches from the person 12. The strength of the negative magnetic field 20 can be varied to allow the magnets 18 to be positioned at a greater distance from the person 12, for example, depending on the thickness of the supporting layer 14 or the magnetic bed device 10. Other contemplated magnetic bed devices or supporting layers may position a person resting thereon about 4–16 inches above the magnets 18, for example.

Figure 3:
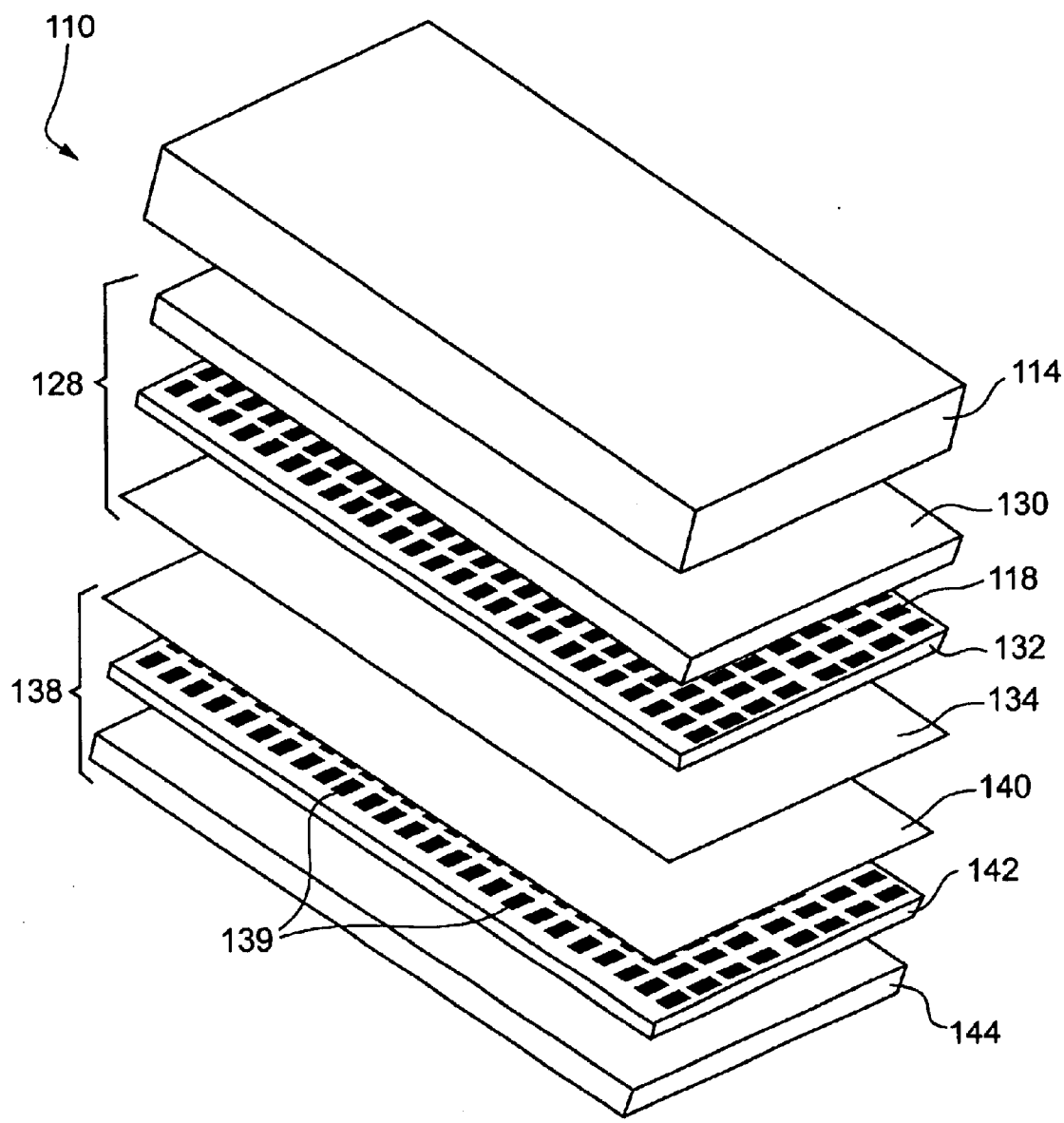
FIG. 3 is a perspective view of another embodiment of the magnetic bed device shown in FIG. 1.
Figure 4:
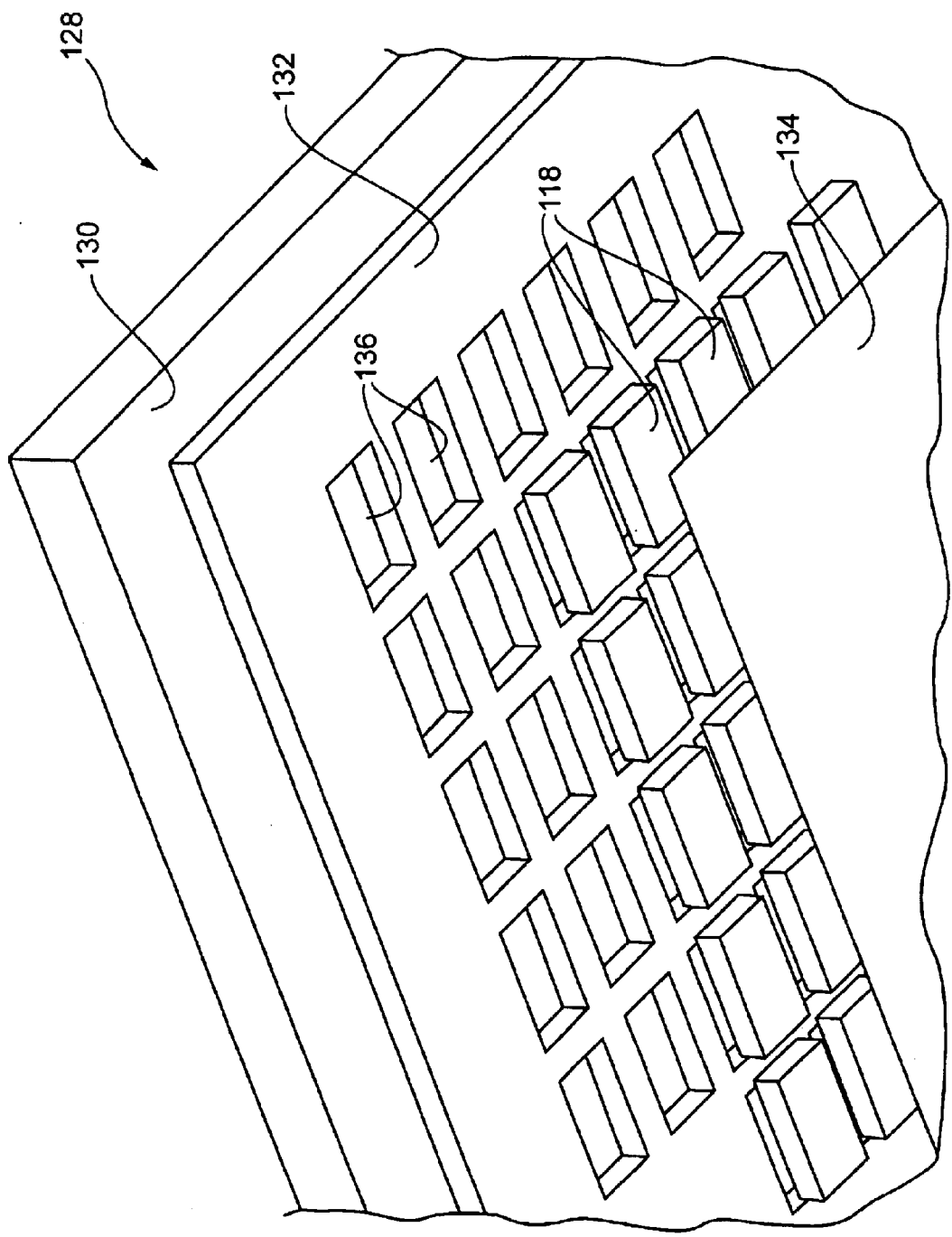
FIG. 4 is a perspective view of the magnets and magnet retaining structure shown in FIG. 1.

FIGS. 3 and 4 show a magnetic bed device in the form of a magnetic bed device 110, which is another embodiment of the magnetic bed device 10 shown in FIG. 1. The magnetic bed device 110 includes a supporting layer 114 and a first magnet retaining structure 128. The first magnet retaining structure 128 comprises a magnet backing layer 130, which may be made of medium density foam, that is positioned adjacent to the supporting layer 114. A magnet retaining layer 132, which is configured to be substantially similar to the magnet retaining structure 24, is positioned adjacent to the magnet backing layer 130 and a magnet cover layer 134 is positioned adjacent the magnet retaining layer 132. The magnet retaining layer 132 is interposed between the magnet cover layer 134 and the magnet backing layer 130. The magnet backing layer 130 and the magnet cover layer 134 can be secured together with adhesive, for example, on opposite sides of the magnet retaining layer 132. The magnet retaining layer 132 includes cutout portions or recessed portions 136, which are each configured to retain one magnet 118 therein (FIG. 4). Although the magnet backing layer 130 and the magnet cover layer 134 secure the magnets 118 in the recessed portions 136, epoxy or another adhesive may be applied to the magnets 118 to further secure the magnets 118 within the cutout portions or recessed portions 136.

Figure 5:
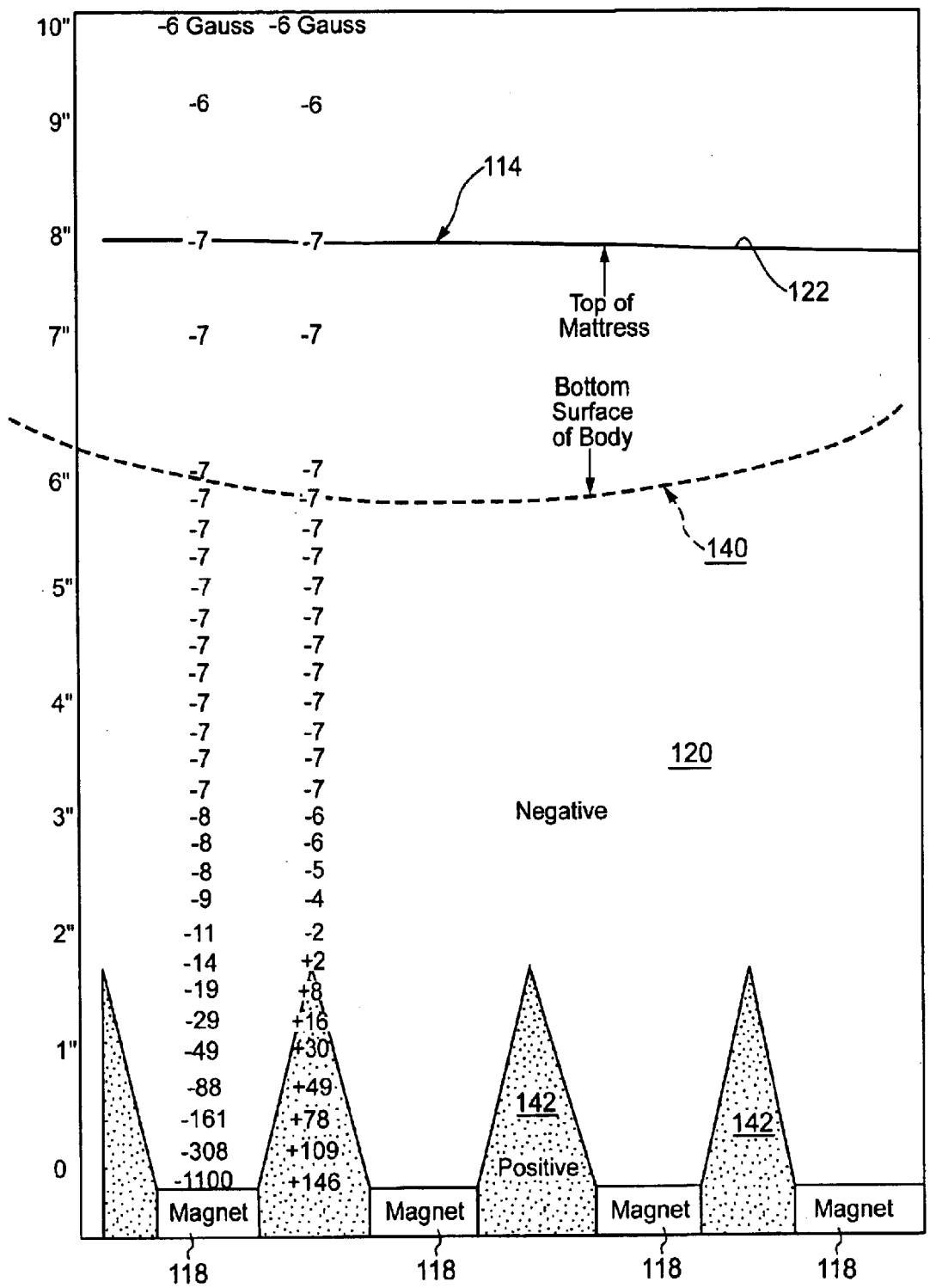
FIG. 5 is an illustrative diagram showing a magnetic field configuration provided by the magnets shown in FIG. 4.

FIG. 3 further shows the magnetic bed device 110 including a second magnet retaining structure 138 that is configured to retain a plurality of magnets 139 therein. The second magnet retaining structure 138 and the magnets 139 are substantially identical in configuration and operation as the magnet retaining structure 128 and the magnets 118, respectively. The second magnet retaining structure 138 is positioned adjacent to the first magnet retaining structure 128 so that the magnets 118, 139 of each respective magnet retaining structure 128, 138 cooperate to provide a negative magnetic field 120 (FIG. 5). The magnets 118, 139 are vertically spaced from one another by an appropriate distance to provide the negative magnetic field 120 of appropriate strength and configuration. For example, the magnets 118, 139 can be positioned as close to one another as possible, about 1/16 inch apart, with a combined thickness of two magnet cover layers 134, 140, which will be described further below.

By positioning the second magnet retaining structure 138 beneath the first magnet retaining structure 128, Applicant has found that this configuration gives the strongest magnetic field per number, strength and size of magnets when the magnets are positioned close to one another, for example, stacked on top of one another.

The second magnet retaining structure 138 comprises a magnet cover layer 140 that is positioned adjacent the magnet cover layer 134. A magnet retaining layer 142 is positioned adjacent the magnet cover layer 140 and a magnet backing layer 144 is positioned adjacent the magnet retaining layer 142. The magnet retaining layer 142 is interposed between the magnet backing layer 144 and the magnet cover layer 140. The magnet backing layer 144 and the magnet cover layer 140 can be secured together with adhesive, for example, on opposite sides of the magnet retaining layer 142. The magnet retaining layer 142 includes recessed portions (not shown, but substantially identical to the recessed portions 136), which are each configured to retain one magnet 139 therein. Although the magnet backing layer 144 and the magnet cover layer 140 secure the magnets 139 in the recessed portions, epoxy or another adhesive may be used to further secure the magnets 139 to further secure the magnets 139 within the recessed portions.

FIG. 5 shows a magnetic field configuration produced through the supporting layer 114 of the magnetic bed device 110 (only magnets 118 are illustrated in FIG. 5) when at least one of the first and second magnet retaining structures 128, 138 are positioned adjacent one another below the supporting layer 114 of the magnetic bed device 110. For example, only one layer of magnets, with each magnet being positioned about 1⅛ inches apart from each another, can be used to produce the magnetic field configuration shown in FIG. 5.

As illustrated, the supporting layer 114 has a thickness of about 8 inches. The magnetic field created by the magnets 118, 139 produces the negative magnetic field 120, which is generally formed in a region adjacent the magnetic bed device surface 122, and a positive magnetic field 142, which is generally formed in the vicinity of the magnets 118. The positive magnetic field 142 is in the form of peaks extending toward the magnetic bed device surface 122. The negative magnetic field 120 is configured to prevent the person from experiencing the positive magnetic field 142. That is, a bottom surface of the person's body, as represented by reference numeral 140, is disposed above the highest extending portion of the positive magnetic field 142.

In general, a spaced magnet array will produce a field such that the negative magnetic field 120 and the positive magnetic field 142 are alternately disposed throughout the supporting layer 114 such that the positive magnetic field 142 is formed between adjacent magnets 118 and the negative magnetic field 120 is formed above the magnets 118 and the person's bottom surface 140.

Figure 6:
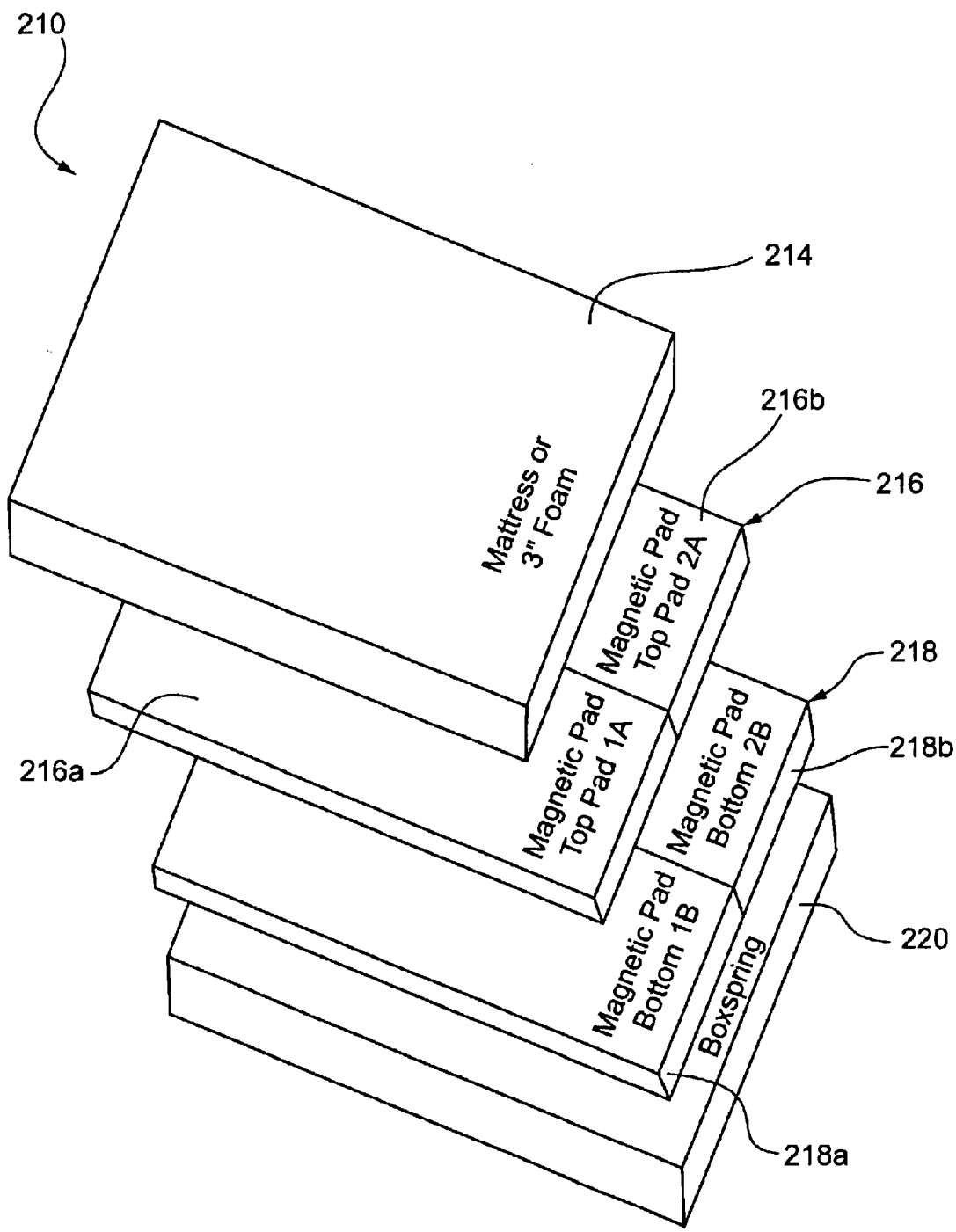
FIG. 6 is a perspective view of yet another embodiment of the magnetic bed device shown in FIG. 1.

FIG. 6 shows a magnetic bed device in the form of a magnetic bed device 210 and magnetic pads 216, 218 supported by a boxspring 220. The magnetic bed device 210 includes a supporting layer 214, which can be made of foam or some other spacing material having a certain depth, such as, for example, at least 3 inches. In this embodiment, as with other embodiments of the invention, the supporting layer may constitute a portion of the magnetic bed device. An upper magnetic layer (magnetic pad) 216 is provided adjacent the supporting layer 214 and a lower magnetic layer (magnetic pad) 218 is provided adjacent the upper magnetic layer 216. The boxspring 220 is provided adjacent the lower magnetic layer 218 to support the supporting layer 214, the upper magnetic layer 216 and the lower magnetic layer 218.

When the weights of the upper and lower magnetic layers 216, 218 are too great to handle easily, each of the magnetic layers 216, 218 can be formed to include mating halves 216a, 216b and 218a, 218b, respectively, having magnets, such as magnets 118, 139. The magnets can be oriented in each mating half 216a, 216b, 218a, 218b to provide a uniform negative magnetic field, such as the negative magnetic field 120 shown in FIG. 5. The mating halves 216a, 216b and 218a, 218b allow a user to easily manipulate and position the upper and lower magnetic layers 216, 218 on the boxspring 220, for example. The mating halves 218a, 218b are positioned adjacent one another on the boxspring 220 and the mating halves 216a, 216b are positioned adjacent one another on the mating halves 218a, 218b, respectively. In another contemplated embodiment, support structures (not shown) could be provided to retain the respective mating halves 216a, 216b and 218a, 218b in adjacent relationship to one another.

Although not shown in the embodiment shown in FIG. 3, the magnet retaining structures 128, 138 could be formed from mating halves to allow for easier manipulation and positioning of the magnet retaining structures 128, 138. Also, the magnet retaining structures 128, 138, which form magnetic layers, could be contained in the supporting layer 114 if placed a sufficient distance, for example, about four inches, from the magnetic bed device surface to allow for body weight compression of the supporting layer thus keeping the body above positive peeks.

Further, a boxspring, similar to boxspring 220, could be provided beneath the supporting layer 14 shown in FIG. 1 or the magnet backing layer 144 shown in FIG. 3 for additional support for the magnetic bed devices 10, 110, respectively.

Although the embodiments have been described hereinabove with respect to implementing one magnetic layer or two magnetic layers, it should be understood that any number of magnetic layers may be implemented in the magnetic bed devices 10, 110, 210 and the magnetic pads 216, 218. The embodiments described herein are not limited to magnetic bed devices or magnetic pads that provide only one or two magnetic layers.

Figure 8:
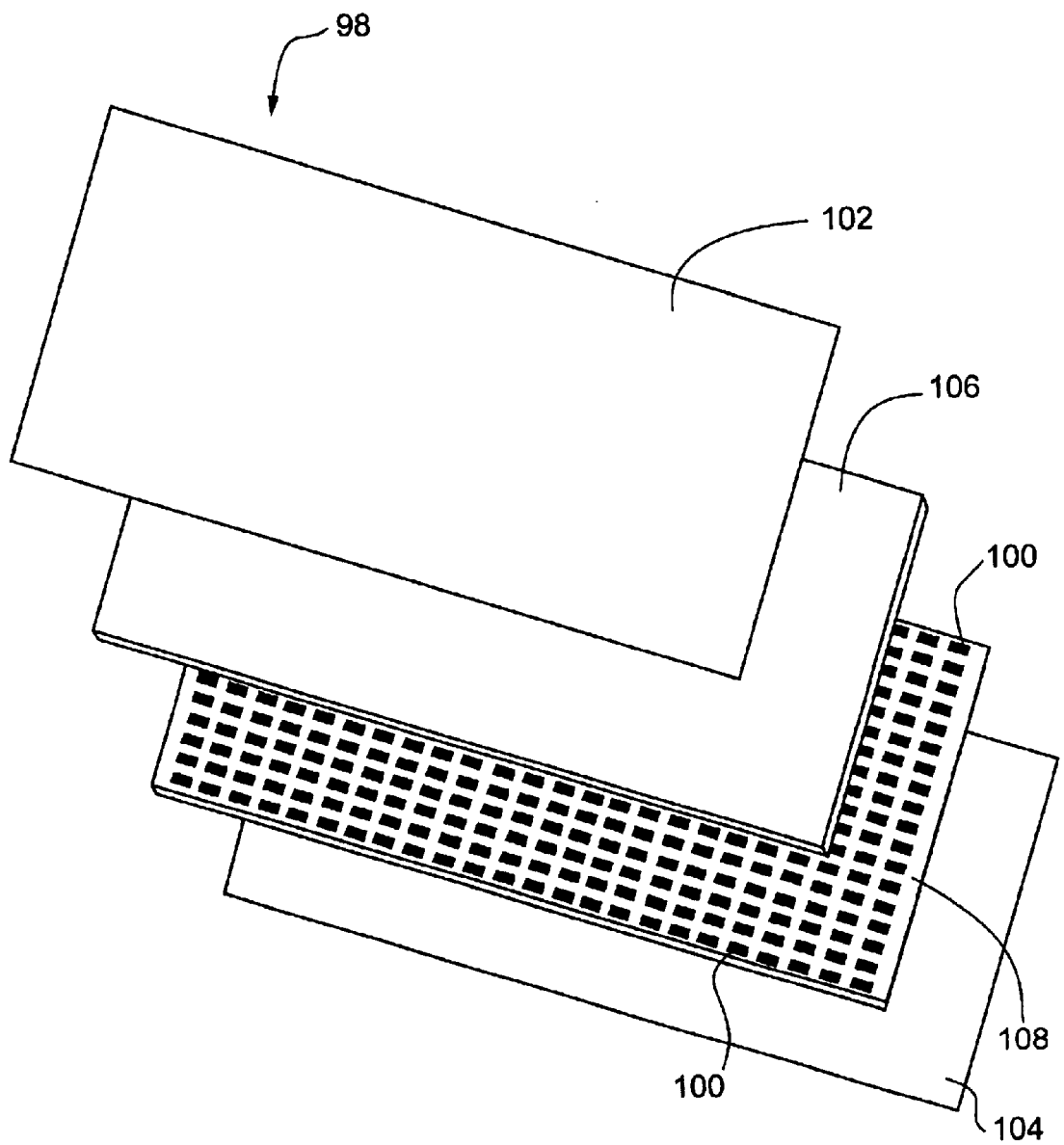
FIG. 8 is a perspective view of a prior art magnetic bed device having magnets provided therein.
Figure 9:
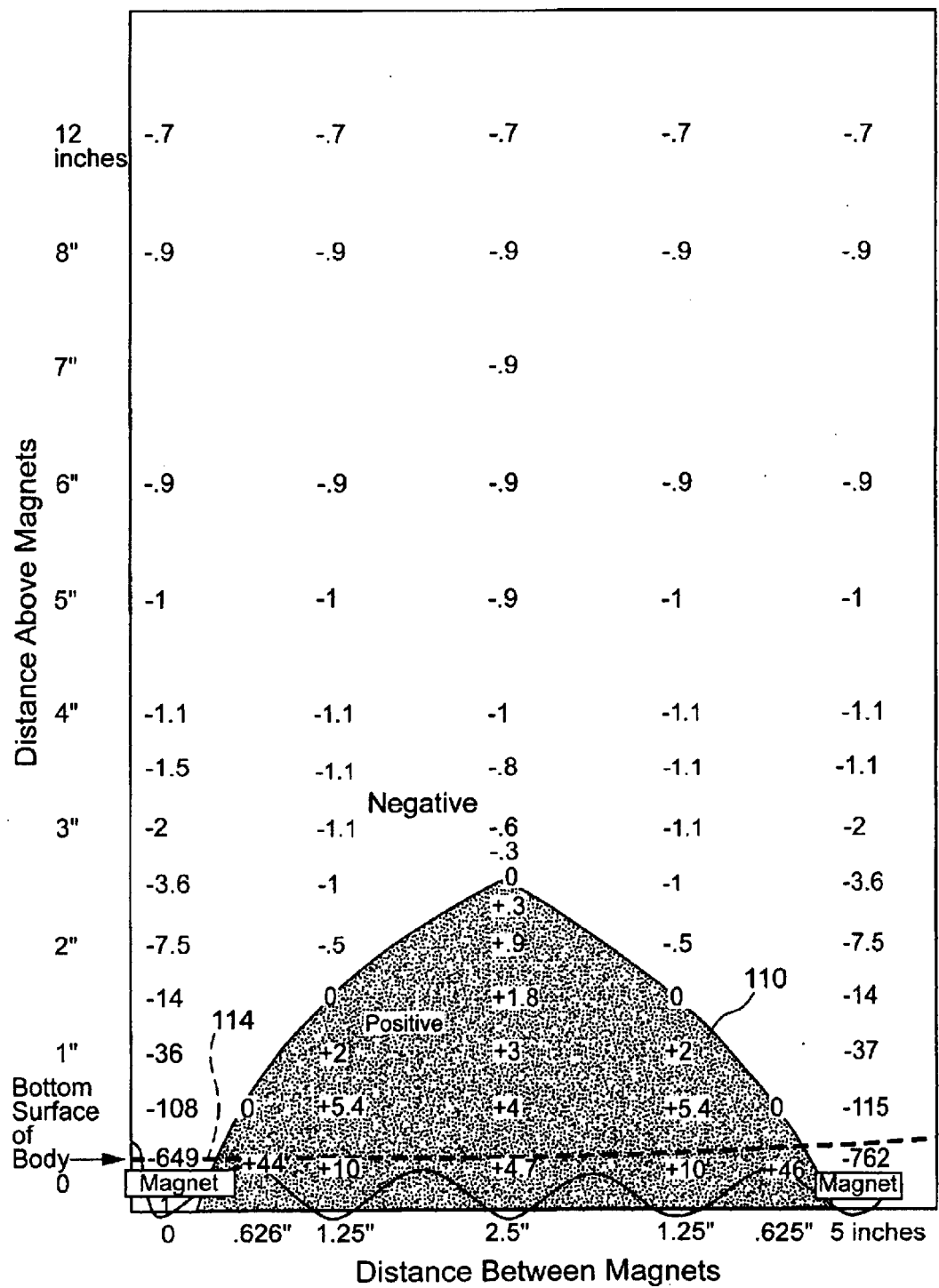
FIGS. 9 and 10 are illustrative diagrams showing respective magnetic field configurations provided by prior art magnet assemblies in magnetic bed devices.
Figure 10:
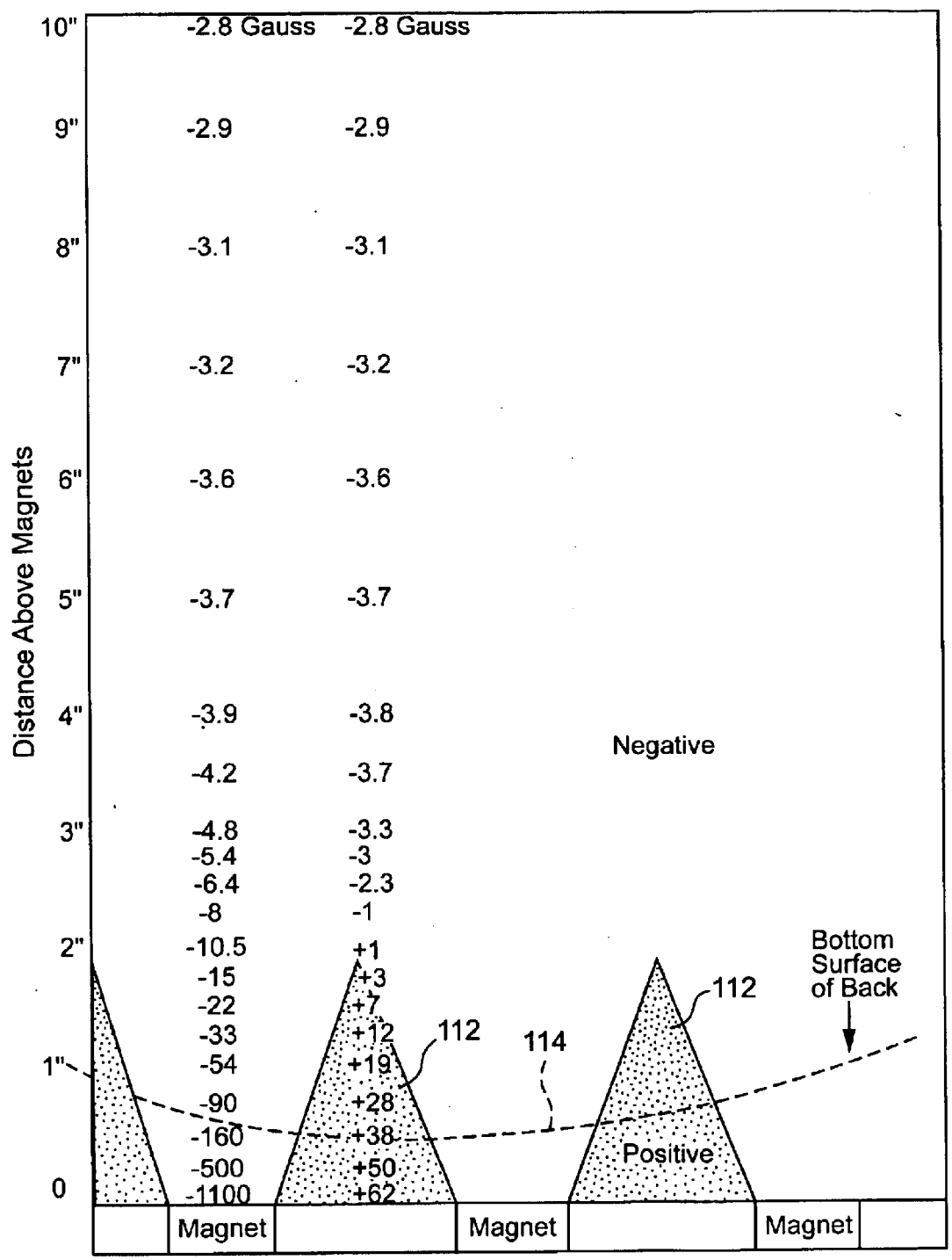

There are various techniques for treating disease of persons using beds with static magnetic fields. In all such techniques, permanent magnets 100 are provided to be placed in a magnetic bed device 98 (FIG. 8) which is placed on top of the surface on which a person rests. The magnets 100 are substantially surrounded by top and bottom covers 102, 104, respectively. A piece of foam or other spacing material 106 is sometimes positioned between the magnets 100 and the top cover 102, however, this spacer, if used with the magnetic bed device 98, is not thick enough to prevent positive peaks from entering the person's body. As illustrated, the magnets 100 are widely spaced apart in a foam surrounding 108 and vary in polarity. As a result, the magnetic field polarity alternates due to configuration of the field lines between the magnets 100. Thus, the resting person (i.e., the bottom surface of a person's back, as represented at reference numeral 114 in FIGS. 9 and 10) experiences amounts of positive or reverse flux, (as shown by reference numerals 110, 112 in FIGS. 8 and 9, respectively). Applicant has determined that while positive or reverse flux can be effective on a short term basis, the positive or reverse flux can be counter productive if used on a long term basis because positive or reverse flux is unnatural to the person.

Applicant has discovered that a magnetic bed device 10, 110, 210 in accordance with embodiments of the present invention showed a statistically significant improvement over prior art magnetic bed devices in reducing pain, reducing fatigue, preventing cancer and in treating disease, such as fibromyalgia, osteoporosis and orthopedic injury.

It should be understood that any one of the magnetic bed devices 10, 110, 210 can be used with either normal beds (beds which do not use water or air at least partially to support a resting person) or water beds or air beds (beds which use water or air to at least partially support a resting person) and can be used by a person to supplement that person's mattress and/or boxspring.

For example, the person may already have a mattress such as supporting layer 214 and a boxspring, such as the boxspring 220. Thus, the person could position one or both of the upper and lower magnetic layers 216, 218, for example, between the mattress and the boxspring. As discussed above, the strength of the negative magnetic field produced the upper and lower magnetic layers 216, 218 can be set to several Gauss, for example, based on the distance between the resting person and the magnets 18 and the number and strength of those magnets 18.

Figure 7:
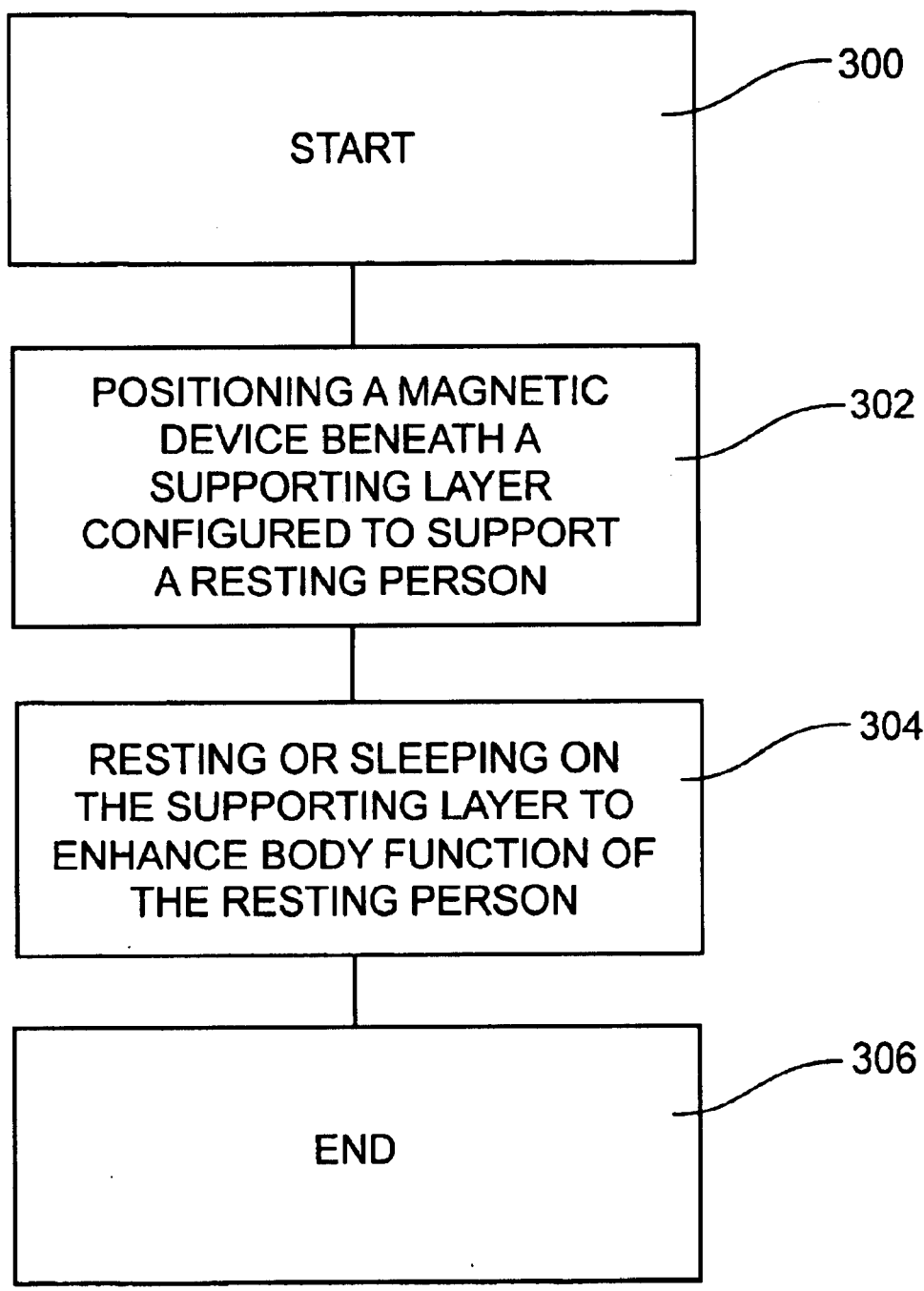
FIG. 7 is an illustrative diagram showing a method of producing a function enhancing field in accordance with the principles of the invention.

In FIG. 7, a method of producing a body function enhancing field is illustrated. At 300, the method begins. At 302, a magnetic device is positioned beneath a supporting layer configured to support a resting person. The magnetic device comprises a plurality of magnets that produce a negative magnetic field in a region adjacent the surface of the supporting layer, and a positive magnetic field in a region remote from the supporting layer surface. The plurality of magnets is positioned relative to the supporting layer such that only the negative magnetic field extends beyond the supporting layer to the resting person. At 304, the resting person may be positioned on the supporting layer to enhance their body function. At 306, the method ends.

The resting person does not necessarily have to be positioned on the supporting layer to practice the method in accordance with the principles of the invention. For example, the method could only include positioning a magnetic device beneath a supporting layer, such as a mattress, configured to support a resting person such that only a negative magnetic field extends beyond the supporting layer. The magnetic device could comprise a plurality of magnets that produce the negative magnetic field.

Any magnetic device comprising a plurality of magnets that produce a negative magnetic field in a region adjacent the surface of the supporting layer, and a positive magnetic field in a region remote from the supporting layer can be used to practice the described method, including the magnetic bed devices 10, 110 or 210.

While the invention has been described with reference to certain illustrated embodiments, the words which have been used herein are words of description rather than words of limitation. Changes may be made, within the purview of the appended claims, without departing from the scope and spirit of the invention is its aspects. Although the invention has been described herein with reference to particular structures, acts and materials, the invention is not to be limited to the particulars disclosed, but rather extends to all equivalent structures, acts, and materials, such as are within the scope of the appended claims.

What is claimed is:

1. A magnetic bed device configured to support a resting person, the magnetic bed device comprising:
    a supporting layer having a surface configured to support the resting person; and
    a magnetic device comprising a plurality of magnets that produce a negative magnetic field in a region adjacent the surface, and a positive magnetic field in a region remote from the surface, the plurality of magnets being positioned relative to the surface such that only the negative magnetic field extends beyond the supporting layer adapted to support the resting person.

2. A magnetic bed device as in claim 1, wherein the plurality of magnets comprises permanent magnets or electromagnets.

3. A magnetic bed device as in claim 1, wherein the magnetic device further comprises resilient material constructed and arranged to provide a supporting force such that the resting person is supported above a highest extending portion of the positive magnetic field.

4. A magnetic bed device as in claim 3, wherein the resilient material is in the form of a plurality of springs.

5. A magnetic bed device as in claim 3, wherein the magnetic device further comprises
    a first magnet retaining structure configured to retain a first portion of the plurality of magnets therein, the magnet retaining structure being positioned adjacent the supporting layer.

6. A magnetic bed device as in claim 5, wherein the first magnet retaining structure comprises:
    a first magnet backing layer positioned adjacent the supporting layer;
    a first magnet retaining layer positioned adjacent the first magnet backing layer and configured to retain the portion of magnets; and
    a first magnet cover layer positioned adjacent the first magnet retaining layer, such that the magnet retaining layer is interposed between the first magnet cover layer and the first magnet backing layer.

7. A magnetic bed device as in claim 6, wherein the first magnet retaining layer includes a plurality of magnet retaining portions configured to retain the first portion of magnets therein.

8. A magnetic bed device as in claim 1, wherein the magnetic device further comprises
    a second magnet retaining structure, separate from the first magnet retaining structure, configured to retain a second portion of the plurality of magnets therein, the second magnet retaining structure being positioned adjacent the first magnet retaining structure.

9. A magnetic bed device as in claim 8, wherein the second magnet retaining structure comprises:
    a second magnet cover layer positioned adjacent the magnet cover layer;
    a second magnet retaining layer positioned adjacent the second magnet cover layer and configured to retain the another portion of magnets; and
    a second magnet backing layer positioned adjacent the second magnet retaining layer, such that the second magnet retaining layer is interposed between the second magnet backing layer and the second magnet cover layer.

10. A magnetic bed device as in claim 9, wherein the second magnet retaining layer includes a plurality of magnet retaining portions configured to retain the another portion of magnets therein.

11. A magnetic bed device as in claim 9, wherein the second magnet retaining layer is positioned beneath the first magnet retaining layer.

12. A magnetic bed device as in claim 1, wherein the negative magnetic field has a strength of at least 2 gauss.

13. A magnetic bed device as in claim 12, wherein the negative magnetic field has a strength in the range of 5–30 gauss.

14. A magnetic bed device as in claim 1, wherein the magnetic device having the negative magnetic field is configured to enhance an immune system of the person and help treat or prevent disease.

15. A magnetic bed device as in claim 14, wherein the disease includes at least one of cancer, fibromyalgia, pain, fatigue, osteoporosis and orthopedic injury.

16. A magnetic bed device as in claim 1, wherein each magnet of the plurality of magnets is spaced from adjacent magnets by a predetermined distance.

17. A magnetic bed device as in claim 1, wherein each magnet is horizontally spaced from adjacent magnets by one predetermined distance and is vertically spaced from adjacent magnets by another predetermined distance.

18. A magnetic bed device as in claim 1, wherein each magnet of the plurality of magnets has a positive pole and a negative pole and wherein the plurality of magnets are arranged to be unidirectional so that the negative pole of each magnet is adapted to face the resting person.

19. A magnetic bed device as in claim 1, wherein the negative magnetic field is substantially uniform across a top surface of the supporting layer.

20. A magnetic bed device to enhance body function, the magnetic bed device comprising:

a supporting layer configured to support a resting person;

a magnetic field generator disposed within the supporting layer and configured to provide a negative magnetic field configured to prevent a positive or reversed direction of magnetic flux from entering the resting person.

21. A magnetic bed device designed to be placed adjacent to a mattress having a surface configured to support a resting person, the magnetic device comprising:

a plurality of magnets that produce a negative magnetic field in a region adjacent the surface, and a positive magnetic field in a region remote from the surface, the plurality of magnets being positioned relative to the surface such that only the negative magnetic field extends beyond the surface to the resting person.

22. A magnetic bed device as in claim 21, wherein the plurality of magnets comprises permanent magnets or electromagnets.

23. A magnetic bed device as in claim 21, wherein the magnetic device further comprises resilient material constructed and arranged to provide a supporting force such that the resting person is supported above a highest extending portion of the positive magnetic field.

24. A magnetic bed device as in claim 23, wherein the resilient material is in the form of a plurality of springs.

25. A magnetic bed device as in claim 23, wherein the magnetic device further comprises a first magnet retaining structure configured to retain a first portion of the plurality of magnets therein, the magnet retaining structure being positioned adjacent the supporting layer.

26. A magnetic bed device as in claim 25, wherein the first magnet retaining structure comprises:

a first magnet backing layer positioned adjacent the supporting layer;

a first magnet retaining layer positioned adjacent the first magnet backing layer and configured to retain the portion of magnets; and a first magnet cover layer positioned adjacent the first magnet retaining layer, such that the magnet retaining layer is interposed between the first magnet cover layer and the first magnet backing layer.

27. A magnetic bed device as in claim 26, wherein the first magnet retaining layer includes a plurality of magnet retaining portions configured to retain the first portion of magnets therein.

28. A magnetic bed device as in claim 21, wherein the negative magnetic field has a strength of at least 2 gauss.

29. A magnetic bed device as in claim 28, wherein the negative magnetic field has a strength in the range of 5–30 gauss.

30. A magnetic bed device as in claim 21, wherein the magnetic device having the negative magnetic field is configured to enhance an immune system of the person and help treat or prevent disease.

31. A magnetic bed device as in claim 30, wherein the disease includes at least one of cancer, fibromyalgia, pain, fatigue, osteoporosis and orthopedic injury.

32. A magnetic bed device as in claim 21, wherein each magnet of the plurality of magnets has a positive pole and a negative pole and wherein the plurality of magnets are arranged to be unidirectional so that the negative pole of each magnet is adapted to face the resting person.

33. A magnetic bed device as in claim 21, wherein the negative magnetic field is substantially uniform across the surface configured to support a resting person.

34. A method of producing a body function enhancing field, the method comprising:

positioning a magnetic device beneath a supporting layer configured to support a resting person, wherein the magnetic device comprises a plurality of magnets that produce a negative magnetic field in a region adjacent the supporting layer, and a positive magnetic field in a region remote from the supporting layer, and wherein the plurality of magnets is positioned relative to the supporting layer such that only the negative magnetic field extends beyond the supporting layer.

35. A method as in claim 34, further comprising positioning the resting person on the supporting layer with the negative magnetic field.

* * * * *

UNITED STATES PATENT AND TRADEMARK OFFICE
CERTIFICATE OF CORRECTION

PATENT NO. : 6,702,730 B2
DATED : March 9, 2004
INVENTOR(S) : Dean R. Bonlie

It is certified that error appears in the above-identified patent and that said Letters Patent is hereby corrected as shown below:

<u>Title page,</u>
Item [12], replace "Bonile" with -- Bonlie --
Item [76], Inventor, replace "Dean R. Bonile, 109-5421 11$^{th}$ ST N.E., Calgary AB (CA), T2E 6M4" with -- Dean R. Bonlie, 109-5421 11$^{th}$ ST N.E., Calgary AB (CA), T2E 6M4 --.

Signed and Sealed this

First Day of June, 2004

JON W. DUDAS
*Acting Director of the United States Patent and Trademark Office*